(12) United States Patent
Kessler et al.

(10) Patent No.: US 7,373,260 B2
(45) Date of Patent: May 13, 2008

(54) SENSOR INFRASTRUCTURE

(75) Inventors: Seth S. Kessler, Brookline, MA (US); Kristin A. Jugenheimer, Cambridge, MA (US); Aaron B. Size, Cambridge, MA (US)

(73) Assignee: Metis Design Corporation, Cambridge, MA (US)

( * ) Notice: Subject to any disclaimer, the term of this patent is extended or adjusted under 35 U.S.C. 154(b) by 0 days.

(21) Appl. No.: 11/071,129

(22) Filed: Mar. 3, 2005

(65) Prior Publication Data

US 2006/0080048 A1 Apr. 13, 2006

Related U.S. Application Data

(60) Provisional application No. 60/549,668, filed on Mar. 3, 2004, provisional application No. 60/616,748, filed on Oct. 7, 2004, provisional application No. 60/616,705, filed on Oct. 7, 2004.

(51) Int. Cl.
*G01B 5/30* (2006.01)
(52) U.S. Cl. ...................................... 702/35
(58) Field of Classification Search ............ 702/33–36, 702/38–43, 47, 49, 54, 56, 130, 138, 150
See application file for complete search history.

(56) References Cited

U.S. PATENT DOCUMENTS

| 3,963,677 | A | | 6/1976 | Enger ........................ 523/113 |
| 4,890,697 | A | | 1/1990 | Fischer et al. ............. 188/1.11 |
| 4,958,100 | A | | 9/1990 | Crawley et al. ............ 310/328 |
| 5,105,918 | A | | 4/1992 | Hagiwara et al. ......... 188/266.7 |
| 5,195,046 | A | | 3/1993 | Gerardi et al. .............. 364/506 |
| 5,305,507 | A | * | 4/1994 | Dvorsky et al. ............ 29/25.35 |
| 5,739,626 | A | | 4/1998 | Kojima et al. .............. 310/360 |
| 5,774,376 | A | | 6/1998 | Manning .................... 364/508 |
| 6,006,163 | A | | 12/1999 | Lichtenwalner et al. ...... 702/36 |
| 6,370,964 | B1 | | 4/2002 | Chang et al. .......... 73/862.046 |
| 6,475,639 | B2 | | 11/2002 | Shahinpoor et al. ........ 428/614 |

(Continued)

FOREIGN PATENT DOCUMENTS

WO 2006/041513 * 4/2006

(Continued)

OTHER PUBLICATIONS

Bar-Cohen, Y., Emerging NDE Technologies and Challenges at the Beginning of the 3$^{rd}$ Millennium--Part I, *Part II* (13 pgs.) & Part II, *Part I* (12 pgs.), *Materials Evaluation* (1999).

(Continued)

*Primary Examiner*—Michael Nghiem
(74) *Attorney, Agent, or Firm*—Mintz, Levin, Cohn, Ferris, Glovsky and Popeo, P.C.

(57) ABSTRACT

A device for use in detecting an event in a structure includes a sensor encapsulation, the encapsulation containing a sensor, an actuator positioned substantially in-plane to the sensor within the housing and a printed circuit board in communication with at least one of the sensor and the actuator. The printed circuit board includes a microprocessor constructed and arranged to collect data from at least one of the sensor and the actuator, a signal generator constructed and arranged to provide excitation to at least one of the sensor and the actuator, and an amplifier to condition the excitation.

16 Claims, 8 Drawing Sheets

U.S. PATENT DOCUMENTS

| | | | |
|---|---|---|---|
| 6,617,764 B2 | 9/2003 | Sebastian et al. | 310/329 |
| 6,768,312 B2 | 7/2004 | Sun et al. | 324/525 |
| 6,850,788 B2 | 2/2005 | Al-Ali | 600/323 |
| 6,931,173 B1* | 8/2005 | Wang et al. | 385/18 |
| 6,943,484 B2 | 9/2005 | Clark et al. | 310/334 |
| 6,964,201 B2 | 11/2005 | Xu et al. | 73/794 |
| 7,117,742 B2* | 10/2006 | Kim | 73/587 |
| 2003/0009300 A1 | 1/2003 | Giurgiutiu | 702/35 |
| 2004/0126305 A1* | 7/2004 | Chen et al. | 423/447.5 |
| 2004/0151071 A1 | 8/2004 | Kocher | 368/10 |
| 2004/0163478 A1 | 8/2004 | Xu et al. | 73/763 |
| 2005/0011277 A1* | 1/2005 | Gao et al. | 73/826 |
| 2005/0114045 A1 | 5/2005 | Giurgiutiu et al. | 702/35 |
| 2006/0031426 A1* | 2/2006 | Mesarina et al. | 709/220 |
| 2006/0081071 A1* | 4/2006 | Kessler et al. | 73/862.391 |
| 2007/0012111 A1 | 1/2007 | Kim | 73/594 |
| 2007/0240515 A1* | 10/2007 | Kessler et al. | 73/597 |

FOREIGN PATENT DOCUMENTS

| | | | |
|---|---|---|---|
| WO | 2006041513 | * | 4/2006 |

OTHER PUBLICATIONS

Chang, F.K., "Structural Health Monitoring: A Summary Report", *Proceedings of the 2nd International Workshop on Structural Health Monitoring*, Stanford, CA, Sep. 8-10, 1999.

Chaumette, D., "Certification Problems for Composite Airplane Structures", *Proceedings of the 6th International European SAMPE Conference*, pp. 19-28 (1985).

Crawley et al., "Use of Piezoelectric Actuators as Elements of Intelligent Structures", *AIAA J.*, 25(10):1373-1385 (1987).

Hall et al., "The Total Data Integrity Initiative ($TDI^2$) - Structural Health Monitoring, The Next Generation", *Proceedings of the USAF*, 2nd ed., pp. 1-25 (1999).

Huber et al., "The Selection of Mechanical Actuators Based on Performance Indices", *Proc. R. Soc. Lond A.*, 453:2185-2205 (1997).

Kessler et al., "Damage Detection in Composite Materials Using Lamb Wave Methods", *Proceedings of the American Society for Composites, Sep. 9-12, 2001*, Department of Aeronautics and Astronautics, MIT, pp. 1-24.

Kessler et al., "Design of a Piezoelectric-Based Structural Health Monitoring System for Damage Detection in Composite Materials", *Proceedings of the SPIE's 9th International Symposium on Smart Structures and Materials*, Mar. 2002, Department of Aeronautics and Astronautics, MIT, pp. 1-11.

Kessler et al., "Experimental Application of Optimized Lamb Wave Actuating/Sensing Patching for Health Monitoring of Composite Stuctures", *Proceedings of the 4th International Workshop on Structural Health Monitoring*, Sep. 15-17, 2003, pp. 1-8.

Kessler et al., "In-Situ Damage Detection of Composites Structures Using Lamb Wave Methods", *Proceedings of the 1st European Workshop on Structural Health Monitoring, Jul. 2002*, Paris, France, pp. 1-9.

Kessler et al., "In-Situ Sensor-Based Damage Detection of Composite Materials for Structural Health Monitoring", *Proceedings of the AIAA/ASME 43rd Structures, Structural Dynamics and Materials Conference*, Apr. 2002, American Institute of Aeronautics and Astronautics, pp. 1-11.

Kessler et al., "Optimization of Lamb Wave Actuating and Sensing Materials for Health Monitoring of Composite Structures", *Proceedings of the SPIE's 10th International Symposium on Smart Structures and Materials*, Mar. 3-6, 2003, pp. 1-11.

Kessler et al., "Optimization of Lamb Wave Methods for Damage Detection in Composite Materials", *Proceedings of the 3rd International Workshop on Structural Health Monitoring*, Sep. 12-14, 2001, pp. 1-11.

Kessler, S.S., "Piezoelectric-Based In-Situ Damage Detection of Composite Materials for Structural Health Monitoring Systems", MIT, Ph.D. thesis, Jan. 2002, pp. 1-200.

Kessler et al., "Structural Health Monitoring in Composite Materials Using Frequency Response Methods", *Composites Part B*, v. 33, Jan. 2002, pp. 1-11.

Kessler et al., "Structural Health Monitoring in Composite Materials Using Lamb Wave Methods", *Smart Materials and Structures*, v. 11, Apr. 2002, pp. 1-13.

Khan et al., "Non-Destructive Testing Applications in Commercial Aircrafts Maintenance", NDT.net, 4(6):11 pages (1999).

Lamb, H., "On Waves in an Elastic Plate", *Proceedings of the Royal Society of London*, Part A: Containg Papers of a Mathematicl and pHysical Character, 93(651):114-128 (1916).

Neumair, M., "Requirements on Future Structural Health Monitoring Systems", *Proceedings of the 7th RTO Meetings*, pp. 11-18 (1998).

Shieh et al., "The Selection of Se'nsors", *Progress in Materials Science*, 46:461-504 (2001).

Srikar et al., "Materials Selection in Micromechanical Design: An Application of the Ashby Approach", *J. Microelectromechan. Systems*, 12(1):3-10 (2003).

Viktorov, I.A., "Rayleigh and Lamb Waves: Physical Theory and Applications", Plenum Press, New York, pp. 1-154 (1967).

Zupan et al., "Actuator Classification and Selection—The Development of a Database", *Advanced Engineering Materials*, 4(12):933-940(2002).

Kessler et al., "Damage Detection in Built-Up Composite Structures Using Lamb Wave Methods", Department of Aeronautics and Astronautics, MIT, pp. 1-29, Jan. 2002.

Kessler et al., "Damage Detection in Composite Materials Using Frequency Response Methods", *Proceedings of the SPIE's 8th International Symposium on Smart Structures and Materials*, Department of Aeronautics and Astronautics, MIT, pp. 1-19, Jan. 2002.

Kessler et al., "Packaging of Structural Health Monitoring Components", MIT, pp. 1-11, Mar. 2004.

Kessler et al., "Selection of Materials and Sensors for Health Monitoring of Composite Structures", pp. 1-10, Dec. 2003.

Kessler et al, "Structural Health Monitoring of Composite Materials Using Piezoelectric Sensors", pp. 1-24, Jan. 2002.

Marantidis et al., "Acoustic-Emission Sensing in an On-Board Smart Structural Health Monitoring System for Military Aircraft", *Proceedings of the SPIE Conference on Smart Structures and Integrated Systems*, 2191:258-264 (1994).

* cited by examiner

SENSOR INFRASTRUCTURE

RELATED APPLICATIONS

This application claims the benefit of priority to United States Provisional Application U.S. Provisional Application Ser. No. 60/549,668 filed on Mar. 3, 2004. This application also claims the benefit of priority to U.S. Provisional Application Ser. No. 60/616,748, filed on Oct. 7, 2004 and U.S. Provisional Application Ser. No. 60/616,705, filed on Oct. 7, 2004, each of which is herein incorporated by reference in its entirety.

GOVERNMENT GRANT

The Government of the United States of America has certain rights in this invention pursuant to contract No. FA9550-05-C-0024 awarded by the Air Force Office of Scientific Research (AFOSR).

FIELD OF THE INVENTION

The invention generally relates to the field of sensing, monitoring, damage detection and structural health monitoring systems defused in aerospace, automotive, naval, civil or other applications.

BACKGROUND OF THE INVENTION

Known methods of laboratory non-destructive structural testing (NDT) methods, such as X-ray detection and C-scans, are impractical for service inspection of built-up structures due to the size and complexity of their infrastructure. Structural Health Monitoring (SHM) involves the incorporation of non-destructive test methods into a structure to provide continuous remote monitoring for damage. SHM systems are systems with the ability to detect and interpret adverse changes in a structure, such as an airplane or other aircraft, automobiles, and naval applications, for example. SHM systems that have been implemented in diverse industries generally include the adhesion of strain gauges or thermocouples to monitor changes in strain, frequency and temperature. Known forms of SHM are "black-boxes" on aircraft that collect critical flight data.

SUMMARY OF THE INVENTION

The invention relates to a damage detection sensor to provide packaged components to facilitate damage detection using a variety of sensors and sensing methods. An embodiment of the invention includes a device for use in detecting an event in a structure, the device comprising a sensor encapsulation, the encapsulation containing a sensor, an actuator positioned substantially in-plane to the sensor within the housing and a printed circuit board in communication with at least one of the sensor and the actuator. The printed circuit board includes a microprocessor constructed and arranged to collect data from at least one of the sensor and the actuator, a signal generator constructed and arranged to provide excitation to at least one of the sensor and the actuator, and an amplifier to condition the excitation.

Implementations of the invention can include one or more of the following features. The sensor can include a sensor that measures at least one of stress, strain, vibration, acoustics, temperature, humidity, pressure, acceleration, location, rotation, radiation, electric fields, magnetic fields, light or motion. The device may include a connector to provide a power and a data connection between the device and a sensor network bus. The connector can include a micro-USB connector. The device may also include a wireless chip positioned in the sensor encapsulation. The device may include a thin film lithium ion battery to supply power to the device. The microprocessor can be configured to collect analog data from at least one of the sensor and the actuator, and further configured to convert the analog data to digital data. The digital data can be stored locally.

Further implementations of the invention may include one or more of the following features. The sensor encapsulation can include an outer cylindrical ring and a lid, and wherein the sensor and the actuator can be positioned in the cylindrical ring. The sensor can be at least one of a geometry including triangular, circular, semi-circular, square, rectangular, octagonal, hexagonal, and pie-shaped. The actuator can be at least one of a geometry including triangular, circular, semi-circular, square, rectangular, octagonal, hexagonal, and pie-shaped. The actuator can substantially completely surround the sensor. The sensor can substantially completely surround the actuator. The device can include a plurality of sensors co-located on at least one piezoelectric wafer, wherein the plurality of sensors are collectively at least partially surrounded by the actuator. The device can include a plurality of actuators co-located on at least one piezoelectric wafer, wherein the plurality of actuators are collectively at least partially surrounded by the sensor. The sensor can provide substantially a 360-degree radial detection of structural occurrences in a material.

In order to practically attain the full economic and design benefits of SHM, several components that amount to sensor infrastructure are integrated into a small package, and an architecture is developed. The components can include a microprocessor to command testing, a function generator to excite actuators, an amplifier to increase signal strength, an acquisition chip to collect data, power, connectors, a communication standard, shielding from electric and magnetic interference, and casing to protect and package the components.

The invention provides one or more of the following capabilities. The damage detection infrastructure can be mass-produced at a low cost, and customized for any application in software. The infrastructure can be broadly defused in aerospace, automotive, naval and civil applications, or any field in which a single sensor or a distributed network of sensors is required to collect data. The infrastructure can be integrated into ageing structures or integrated into newly designed structures. The invention can enable the elimination of scheduled inspections. Structural design can be improved with increased reliability and reduced life-cycle costs. Embodiments of the invention can be constructed without the use of solder and exposed wires. Fewer sensors can accomplish detection without limiting the range over which detecting is desired. Embodiments of the invention can be implemented as a continuously monitoring system, which can require less human intervention. Other capabilities will be apparent upon a review of the Figures and Detailed Description that follows.

DETAILED DESCRIPTION OF THE INVENTION

The features and other details of the invention will now be more particularly described. It will be understood that particular embodiments described herein are shown by way of illustration and not as limitations of the invention. The principal features of this invention can be employed in various embodiments without departing from the scope of the invention.

Embodiments of the invention are directed to concentrically positioned sensors and actuators. Embodiments of the invention can be directed to a piezoelectric-based sensor and actuator for use in facilitating damage detection, non-destructive testing ("NDT") and structural health monitoring ("SHM") using a variety of sensors and sensing methods. Embodiments of the invention can include damage detection systems employing one or more than one piezoelectric damage detector. Embodiments of the invention can be directed to an infrastructure for use in monitoring a structure. Embodiments of the invention relate to a collection of electrical and mechanical components necessary to conduct in-situ damage detection methods. Embodiments of the invention can be implemented as wired systems or as wireless systems. Embodiments of the invention can be used in SHM of aircraft, spacecraft, naval vessels and automobiles. Embodiments of the invention may be used in other structures using sensor networks and to conduct testing procedures other than NDT and SHM procedures. For example, embodiments of the invention can be used for non-destructive evaluation, measurement, usage monitoring (HUMS), security, surveillance, condition monitoring or quality control. Embodiments of the invention can be used for other applications.

Figure 1:
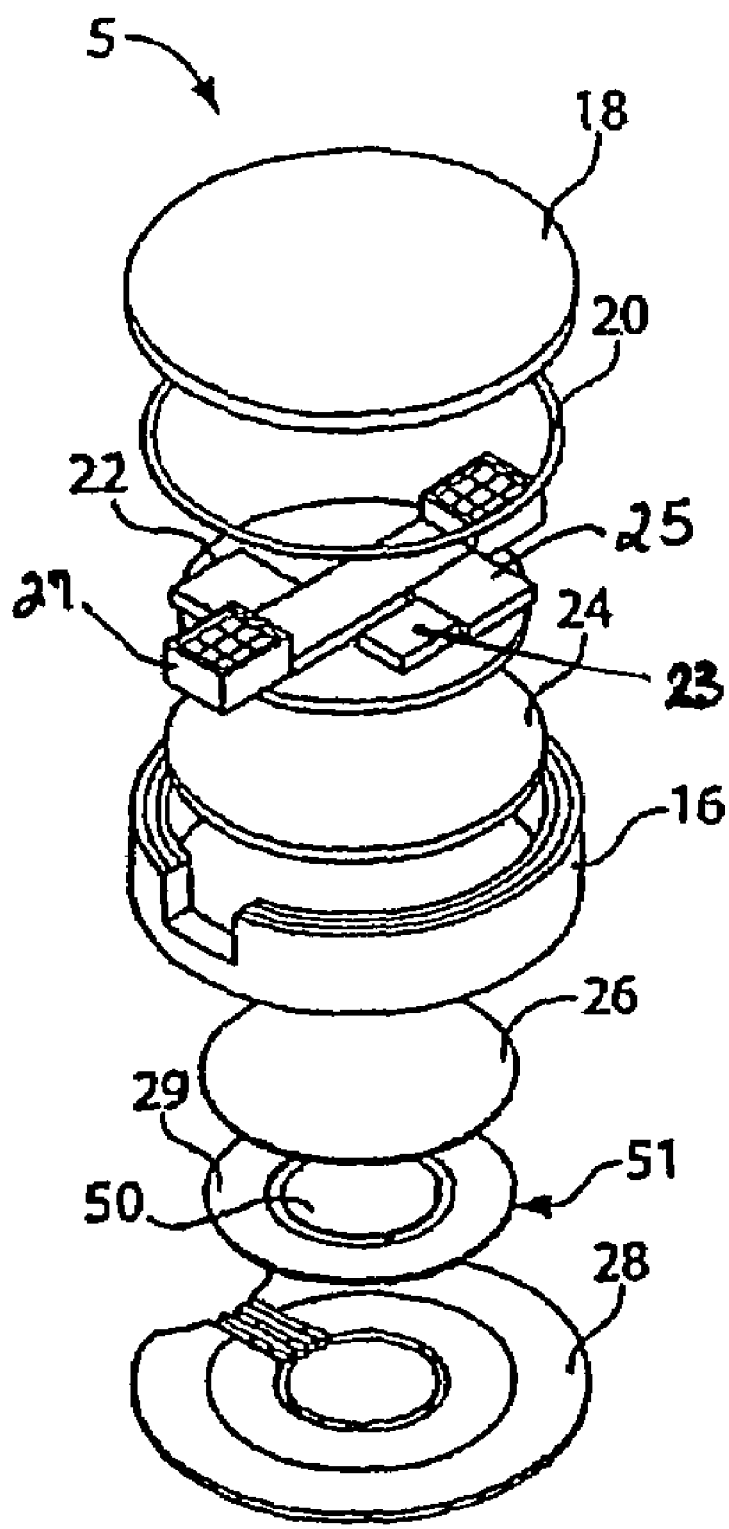
FIG. 1 is an assembly view of a damage detection device.

Referring to FIG. 1, a sensor node 5 includes a top lid 18 having an o-ring 20, a printed circuit board (PCB) 22, a plunger 24, a casing 16, a flexible circuit having a top portion 26 and a bottom portion 28 and a sensor 50 and actuator 51 pair. For purposes of the following, the sensor 50 and actuator 51 pair may also be referred to as a piezoelectric wafer 29. The lid 18 and the casing 16 join to form a housing for the electronic components of the node 5. The PCB 22 is protected by the sealing o-ring 20 and the plunger 24 within the casing 16. The top portion of the flexible circuit 26 is positioned above the piezoelectric wafer 29. The bottom portion 28 is positioned below the wafer 29. The flexible circuit 26 and 28 provides power and data connections to and from the wafer 29. A piezoelectric stack 30 (shown in FIG. 3) includes the flexible circuit 26, 28 and the wafer 29.

The PCB 22 collects data via a connection to the sensor 50. For example, the PCB 22 includes electronic components to collect analog data, convert the analog voltage data to digital data, and locally store the data in a buffer at a high update rate and bit-resolution. Embodiments of the PCB 22 could also collect other analog current or resistance measurements, as well as direct digital signals. The PCB 22 can include an integrated data logger capable of, for example, 1 MHz acquisition on 2 channels of 1000 points per channel, with a dynamic range of 10 mV-10V. The PCB 22 also includes electronic components to facilitate excitation of the sensor 50 or actuator 51 with programmable or fixed arbitrary waveforms. The PCB 22 can contain a signal generator 25 capable of 1 MS/s and 20 Vpp arbitrary function generation of up to 1000 points on 2 channels, for example. An amplifier 27 or other electronic components can be included to condition the signal, such as to condition the excitation and resulting sensor voltages.

The nodes may have a unique nodal address that can be accessed either directly or via the internet in order to collect the critical information regarding the sensor node, including version, date fabricated, design revision, operating, reliability and certification data. Some embodiments of the invention may include a microprocessor 23 within the sensor node 5 located on PCB 22 that can receive command data remotely to initiate damage detection checks, as well as uploading new firmware to control internal components or software to locate and interpret data.

The nodes may have a unique nodal address that can be accessed either directly or via the internet in order to collect the critical information regarding the sensor node, including version, date fabricated, design revision, operating, reliability and certification data. Some embodiments of the invention may include a microprocessor within the sensor node 5 located on PCB 22 that can receive command data remotely to initiate damage detection checks, as well as uploading new firmware to control internal components or software to locate and interpret data.

Figure 2:
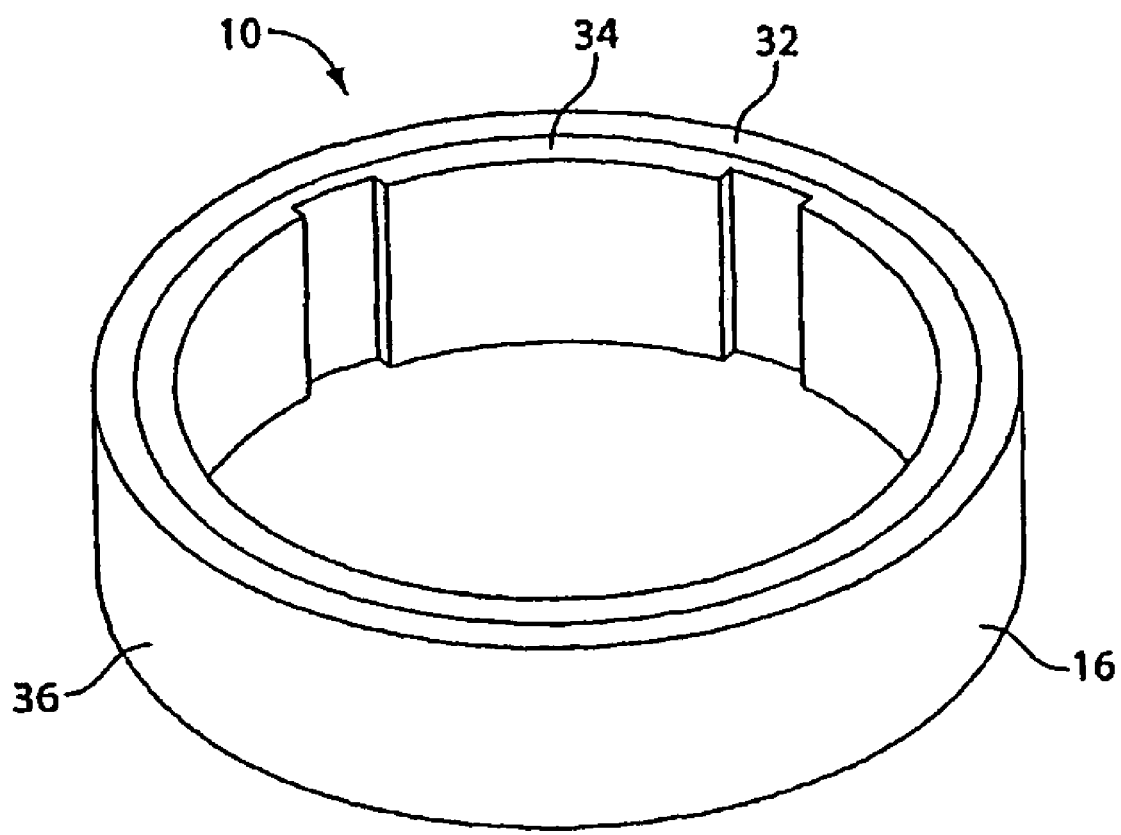
FIG. 2 is a top perspective view of the internal portion of an assembled damage detection device.

Referring to FIG. 2, a housing 10 provides an interface between the sensor 50 and the structure to which the node 5 is connected for monitoring. When assembled, the node 5 is capable of providing an integrated sensing unit for conveying information about a structure. The sensor node including the piezoelectric wafer 29 is assembled in the housing 10. The housing 10 is comprised of the cylindrical casing 16 and the top lid 18. The casing 16 includes the inner o-ring 20 and an o-ring groove 32, a grounding ring 34, mini USB connector and apertures 36. The apertures 36 are positioned to accept micro-connectors, such as connector 12 and connector 14. The USB connector apertures 36 accept USB connectors that complete mating connection with the internal portion of the housing 10 and extend to an external portion of the node 5. The apertures 36 can be positioned on opposite sides of the cylinder 16. The o-ring groove 32 is positioned on a top face of the cylinder 16 and accommodates an o-ring 61. The o-ring 20 provides a seal that is preferably watertight to keep moisture from entering the housing 10.

A top portion of the casing 16 can be threaded on an internal face of the casing 16, for example. The top lid 18 can be a flat portion having a threaded rim to engage with the threads of the cylinder 16. Alternatively, the top lid 18 and the casing 16 can be fitted in a number of known means of closure. The lid 18 can be alternatively designed to complete the housing 10 including glue-on press fits, screw top, and cam-lock, preferably incorporating o-rings to provide a seal.

The housing 10 provides a barrier for the electronic components of the node 5. The housing 10 can include a low moisture absorbing plastic casing. For example, a low density, low moisture absorbing and moldable plastic such as an Acetal (e.g. Delrin) can be used as a casing material.

The housing 10 provides an enclosure to package each component of the infrastructure of the node 5, protecting the components against incidental impact damage, sealing the components from moisture, and isolating the sensor 50 from large induced strains on the structure or cables. The housing 10 can provide additional protections or barriers for node 5. Nominal dimensions for this housing 10 can be, for example, approximately 1.5" in diameter and 0.3" in height with a 0.1" wall thickness, however depending on the nature of the application, the housing 10 can be smaller or larger in any dimension. Preferably, the housing 10 of the detection device has an outer diameter of approximately 1.6 inches and a total volume less than 1 cubic inch. The height of the housing can be approximately 0.5 inches.

The housing 10 is survivable to a large variety of common solvents, including fuels, oils, paint, acetone and cleaning solutions, as well as other chemicals. The housing 10 can operate under thermal conditions between −50° F. and 250° F. The housing 10 may be designed to operate under thermal conditions below −50° F. or above 250° F. The housing 10 containing the node 5 can be adhered to a structure using a thermoset or thermoplastic film adhesive, or by using a traditional epoxy. Other adhesives are possible. The housing 10 is further preferably constructed to withstand a strain of 2000 microstrain and can have a vibration resonance tolerance of 66 Hz or greater.

Figure 3:
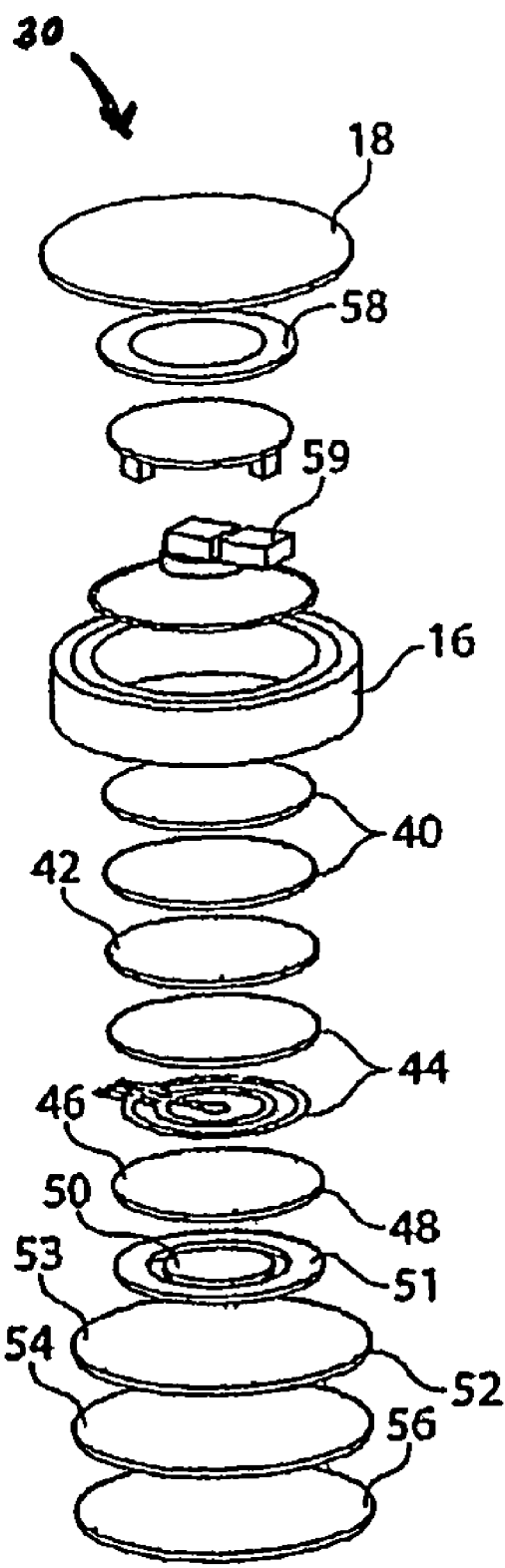
FIG. 3 is an assembly drawing of the piezoelectric stack contained in the casing of a damage detection device.

In an expanded view, in FIG. 3, a piezoelectric stack 30 is contained in the housing 10 and includes a copper-coated Kapton™ shield 40, an adhesive film 42, a copper-coated Kapton™ electrode 44, an electrically conductive adhesive 46, a second film adhesive layer 48, the piezoelectric sensor 50 and actuator 51, a third film adhesive layer 52 having an electrically conductive portion 53, a polyester film layer 54 and a fourth film adhesive layer 56. The copper-coated Kapton™ shield 40 is a layer of copper-coated Kapton™ that provides an insulating surface on the topside and an EMI shield on the underside. The adhesive film 42 can be an insulator capable of bonding to copper-coated Kapton™. For example, the adhesive film 42 can be 3M™ 3132 film adhesive. The copper-coated Kapton™ electrode 44 is a layer of copper-coated Kapton™. The electrode pattern can be created using Ferric Chloride. The copper-coated Kapton electrode 44 provides contacts to both the sensor 50 and the actuator 51. The copper-coated Kapton™ electrode 44 can also provide a shielding ground loop between the sensor 50 and the actuator 51. The ground loop can prevent in-plane parasitic noise. The electrically conductive adhesive 46 and the second film adhesive layer 48 connect the leads to the piezoelectric sensor 50 and actuator 51. The adhesive 46 and the second film adhesive layer 48 can be provided to avoid a short circuit. The third film adhesive layer 52 provides an electrically conductive layer of adhesive and is positioned beneath the sensor 50/actuator 51 layer to provide a common ground. The film layer 54 and the fourth film adhesive layer 56 provide a semi-rigid backing for mounting to a structure that the sensor node 5 is monitoring.

The sensor 50/actuator 51 is controlled by the flexible circuit electrode 44. Adhesive layers between the electrode 44 and the sensor 50/actuator 51 connect each layer of the piezoelectric stack 30. Adhesive layers can be electrically conductive. Alternatively, adhesive layers can connect other layers without electrical conductivity. The piezoelectric sensor 50 measures reflected waves in a material on which the sensor is positioned. Sensors can record, for example, variables such as strain, acceleration, sound waves, electrical or magnetic impedance, pressure or temperature. The actuator 51 excites waveforms in a material to create reflected waves that the sensor 50 measures.

The node 5 can be used as a wireless device, as shown in FIG. 3. In FIG. 3, the housing 10 includes a wireless transceiver or chip 58 and a battery 59. The transceiver 58 receives commands and transmits data. The battery 59 can be a rechargeable thin-film Lithium ion polymer battery to provide power. A wireless inductive loop or energy harvesting may be used to recharge the battery 59. As described, however, the sensor node 5 can be used as a wired embodiment. The sensor infrastructure used in a wired system includes a communication standards chip, either USB, RS485 or CAN bus, and a mini-USB connector to provide power and digital data transfer, all of which is contained on the PCB 22, for example, as described with respect to FIG. 1.

Figure 4A:
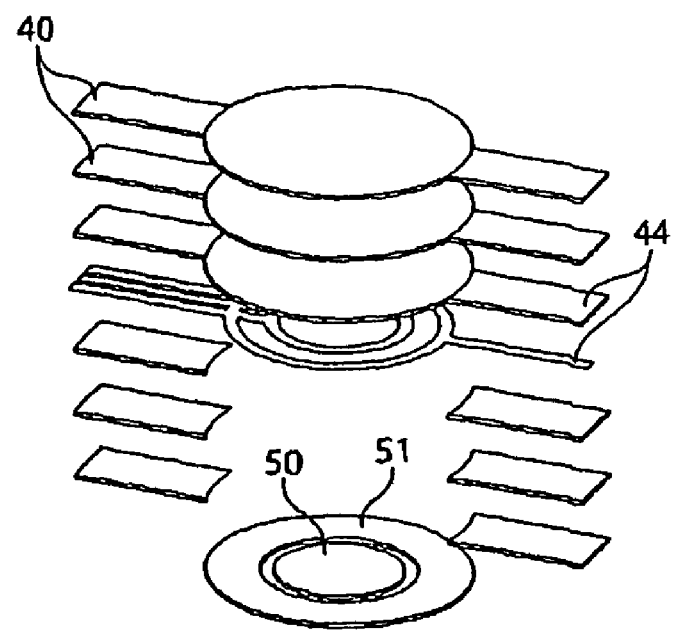
FIG. 4A is a portion of the piezoelectric stack of FIG. 3.
Figure 4B:
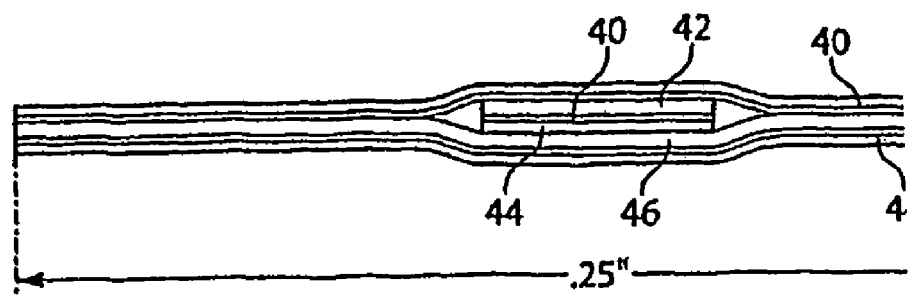
FIG. 4B is a side perspective view of a portion of the piezoelectric stack of FIG. 3.

FIG. 4A is an exploded assembly view showing each of the layers of the flexible circuit surrounding the piezoelectric elements. Included are a conducting layer on top with a shield layer above that, and a bottom grounding layer. Also displayed are the layered wings that carry the power and sensor signal with shields on either side. FIG. 4B is a collapsed assembled version of FIG. 4A.

The electrode flexible circuit, shown in FIG. 4A, controls the sensor 50 and actuator 51. The electrode flexible circuit is positioned above the sensor 50/actuator 51 layer. Each of the layers of the flexible circuit is connected by the contact of the side tabs, shown in FIG. 4B. The flexible circuit 180 provides electrical connections. A copper-coated Kapton™ element is printed so that there are separate grounds for the actuator and sensor, and separate ground traces to provide in and out-of-plane signal shielding. Wings on the side of the flexible circuit 180 fold up. The wings can provide an electrical connection in a substantially convenient location during manufacture and integration. The wings are shielded in and out-of-plane. The wings terminate in heat bonded or soldered connections with the PCB 22, and serve to transfer power and data to and from the PCB 22 to the sensor 50/actuator 51 layer.

Figure 5A:
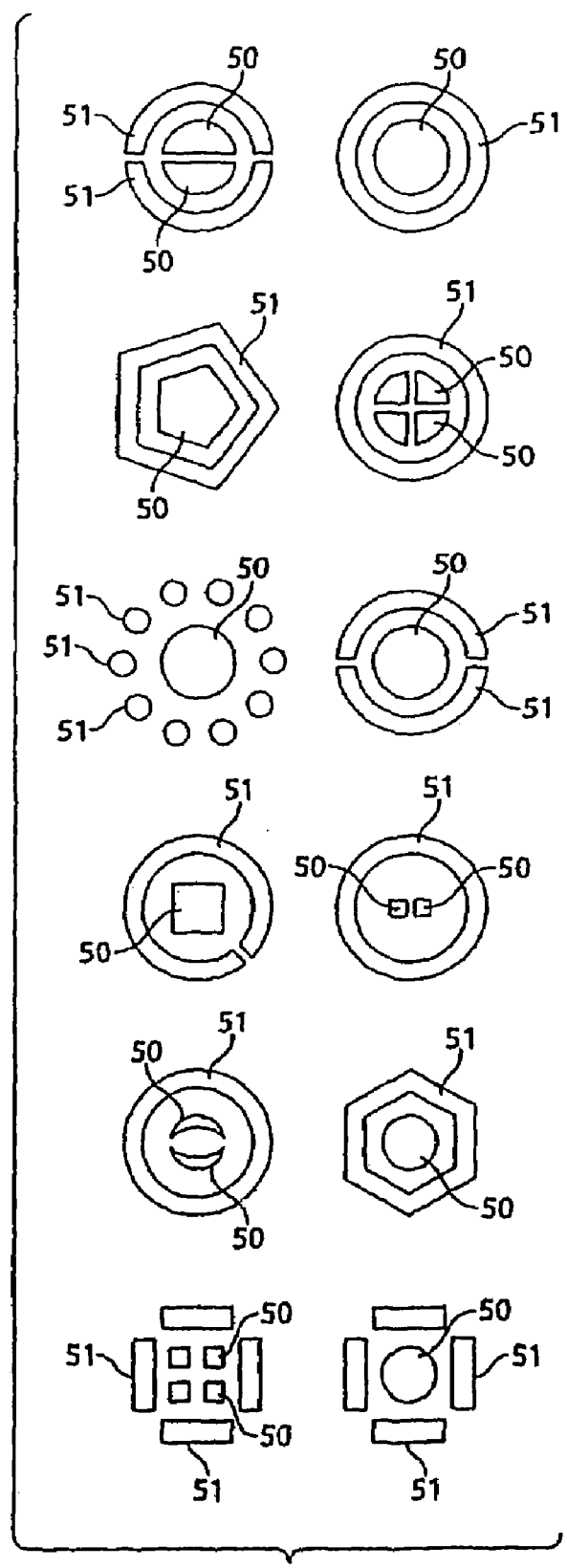
FIG. 5A includes alternative geometries for a sensor substantially surrounded by an actuator.

The sensor 50/actuator 51 layer of the node 5 comprises a concentric, circular sensor 50 having an outer ring comprising the actuator 51. The sensor 50 and the actuator 51 are in-plane components capable of connection to the circuit without the use of wires. Referring to FIG. 5A, the in-plane sensor 50 and actuator 51 can be a number of alternative shapes. For example, the sensor 50 can be circular, semi-circular, square, triangular, rectangular, pie-shaped, hexagonal, octagonal, and any of a number of other shapes. The actuator 51 can also be any of a number of shapes configured to substantially surround the sensor 50. The substantially concentric design of the sensor 50 and actuator 51 provide omni-directional operation of the node 5. The substantially concentric design of the sensor 50 and actuator 51 provide a pulse/echo method of sensing. By having an actuator that surrounds a sensor or set of sensors (or vice versa) this allows excited signals (electrical, magnetic, acoustic, vibrational or otherwise) to be emanated omni-directionally from a nearly point source, and for response measurements to be taken from nearly the same location.

Figure 5B:
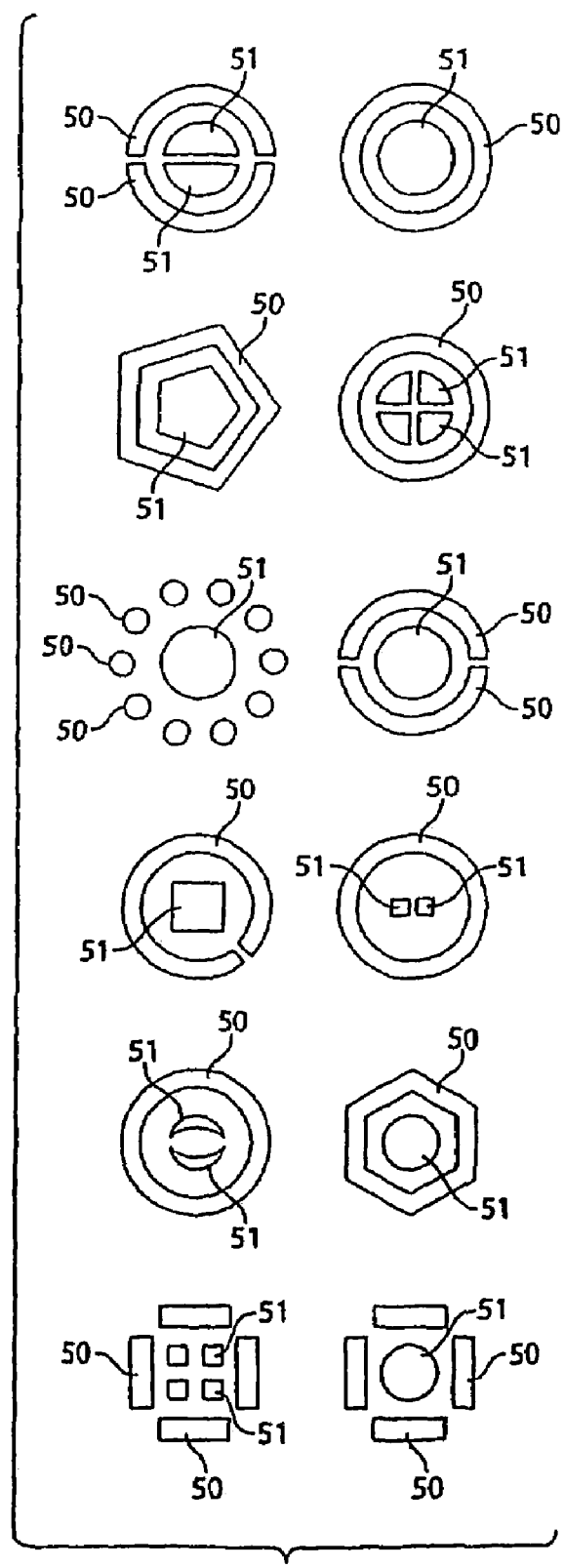
FIG. 5B includes alternative geometries for an actuator substantially surrounded by a sensor.

Each of the sensor 50 and the actuator 51 can surround, or substantially surround the other. In each of the alternative configurations shown in FIG. 5B, the center portion can be the actuator 51, surrounded by one or more than one sensor 50. Thus, a sensor or a set of sensors can be surrounded by an actuator or a set of actuators. Alternatively, an actuator or a set of actuators can be surrounded by a sensor or a set of sensors in the concentric design. In some systems, at least one of the piezoelectric nodes includes a sensor 50 surrounded by an actuator 51, and at least one of the piezoelectric nodes includes an actuator 51 surrounded by a sensor 50 where each of the nodes works in tandem with the other or others to accomplish material sensing.

The in-plane configuration of the actuator 51/sensor 50 pair achieves contact with a material to be monitored or tested using thermoset or thermoplastic tape, epoxy, using a couplant material, or with an externally applied force. Other room temperature or elevated cure methods of contact are possible and envisioned. In some applications, the sensor 50 and actuator 51 pair are not encapsulated in a housing 10, but are substantially directly positioned on a material or structure for use. The actuator 51/sensor 50 pair can be actuated with an electrical or magnetic field being applied so as to excite through-thickness, axial, shear or radial modes in the actuator. This field can be applied to a parallel face of the actuator 51, or using interdigitated electrode patterns. Sensor voltage data can be measured using any of these fields. Preferably, the sensor 50 and actuator 51 are constructed of a piezo-ceramic material. Other known materials can be used, however, such as other piezoelectric materials (PVDF, PMA, etc), piezoresistive materials or magnetorestrictive materials, for example. A variety of other sensor may be used within the infrastructure, including, but not limited to sensors that measure, stress, strain, temperature, moisture, acceleration, motion, radiation or electrical and magnetic fields.

The sensor 50/actuator 51 pair can comprise a single piezoelectric wafer, or more than one piezoelectric wafer. The particular piezoelectric material used for the wafer 29 can be PZT-5A in order to reduce the dependency of performance on temperature, however other grades of PZT such as PZT-5H would also be acceptable. The piezoelectric elements are either injection molded, machined or microfabricated in either addition or subtraction processes into the desired geometry, typically less than 1" in diameter. Other dimensions are possible and envisioned, and may vary depending on optimizing an application.

Sensors 50 embodied in nodes 5 are used in an infrastructure to monitor defects in a material or structure. One or more than one node 5 can be used. A variety of sensor types can be placed into an infrastructure together or separately, including, but not limited to, sensors that measure stress, strain, vibration, acoustics, temperature, humidity, acceleration, radiation, electric or magnetic fields, light and/or motion. Further, infrastructure systems of nodes 5 can be surface-mounted or embedded for applications that include, for example, structural health monitoring, non-destructive evaluation, health usage monitoring, surveillance or security.

Figure 6A:
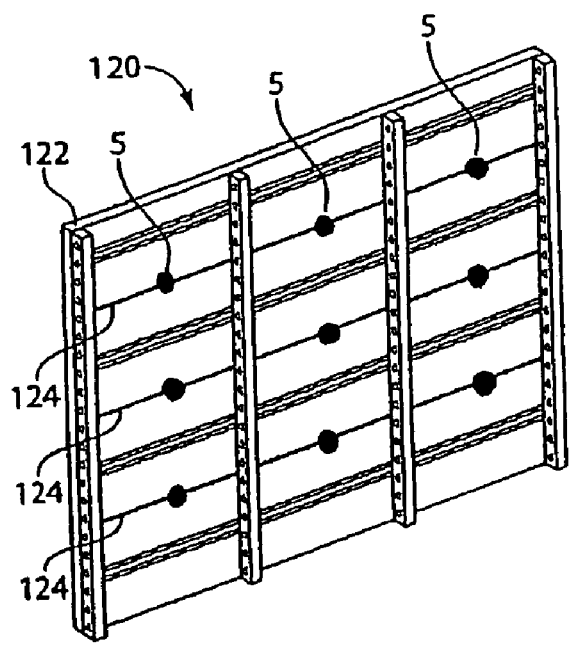
FIG. 6A is a schematic of a wired system attached to a structure.
Figure 6B:
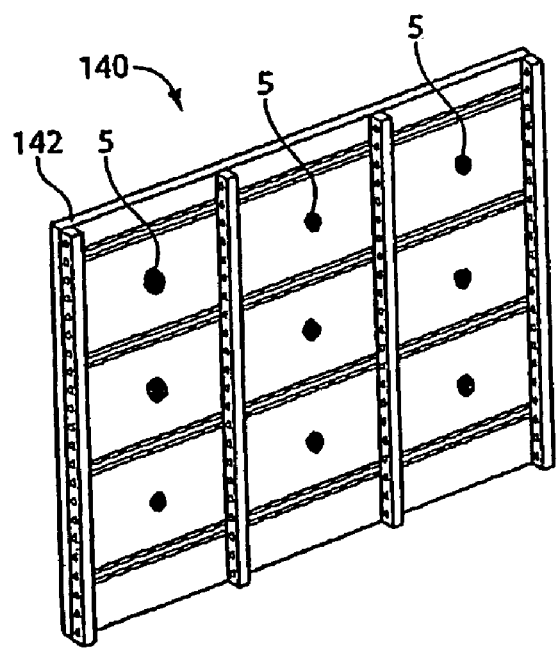
FIG. 6B is a schematic of a wireless system attached to a structure.

Referring to FIGS. 6A and 6B, one or more than one node 5 can be positioned in a system or structure to detect damage in a material or structural configuration. In FIG. 6A, a wired damage detection architecture 120 is positioned in a structure 122. For example, the structure 122 can be a panel in the body of an airplane. The nodes 5 are positioned throughout the structure 122. Connectors 124 allow communication between nodes 5.

In FIG. 6A, a "wired" version of an infrastructure includes a communication standard chip to provide power and digital data transfer between a central computer, which controls each node in the system, and the sensor infrastructure. This is achieved by using a USB, RS485 or CAN bus. Other embodiments that support digital data transfer over long distances are also possible. A mini-USB connector is used to mount the PCB 22 into the housing 10, and to connect each sensor node 5 to each other and to the central processor. The wired nodes 5 can be daisy chained to each other to transfer data or power, or connected to a computer USB port through a protocol adapter. The sensors can be daisy-chained in order to reduce cable length, complexity and cost, as well as for other purposes. For larger structures, clusters of nearby sensor nodes are daisy chained, and connected to a hub, then relayed to the central processor, which is the computer that collectively controls each node in the system, where a node is defined as a single sensor infrastructure unit.

Internally, the electronic components of the sensor infrastructure are connected to mini-USB connectors on either side of the sensor node to facilitate CAN bus connectivity and daisy chaining to the nearest neighbor node. The standard USB 10 Vpp power supply is used, as well as a standard USB cable, however other suitable cable may be used to support various harsh and specialized conditions. The damage detection sensors can be surface mounted on structures in which health monitoring is conducted. Alternatively, the damage detection sensors can be embedded into structures to accomplish health monitoring.

Referring to FIG. 6B, nodes 5 are positioned throughout a structure 142. The wireless version 140 of the infrastructure includes a wireless transceiver to receive commands and transmit data, and may not have a need for any other type of connector. Software and firmware can be remotely loaded onto the microprocessor using the wireless protocol. The wireless nodes 5 can pass information to the nearest neighbor nodes, or other nearby nodes, in a "fire brigade" fashion until the data reaches the central processor. The data can be passed from node to node redundantly.

Damage detection methods use the wired or the wireless infrastructure to determine the presence of damage in a structure. Damage detection methods may also be used to determine the size, shape, type, location and extent of damage in a structure or material, as well as the criticality of maintenance, repair or replacement. For example, methods include lamb waves, modal analysis, acoustic emission, strain/stress monitoring, temperature and acceleration measurement. Each of the damage detection methods can use a single actuator 51/sensor 50 pair measuring at different frequencies and time samples. Methods of detection can be accomplished by changing frequency of actuation, frequency of acquisition and filters. Further, the use of passive methods (such as strain and/or acoustic emission) to trigger active methods (such as frequency response and lamb waves) can be used to conserve power. Active modes can be used at set intervals or upon user command tests. Methods of detection can include intermittent active methods, which can seek detailed information. Passive methods can be listening for events that can trigger active methods of detection.

Figure 7:
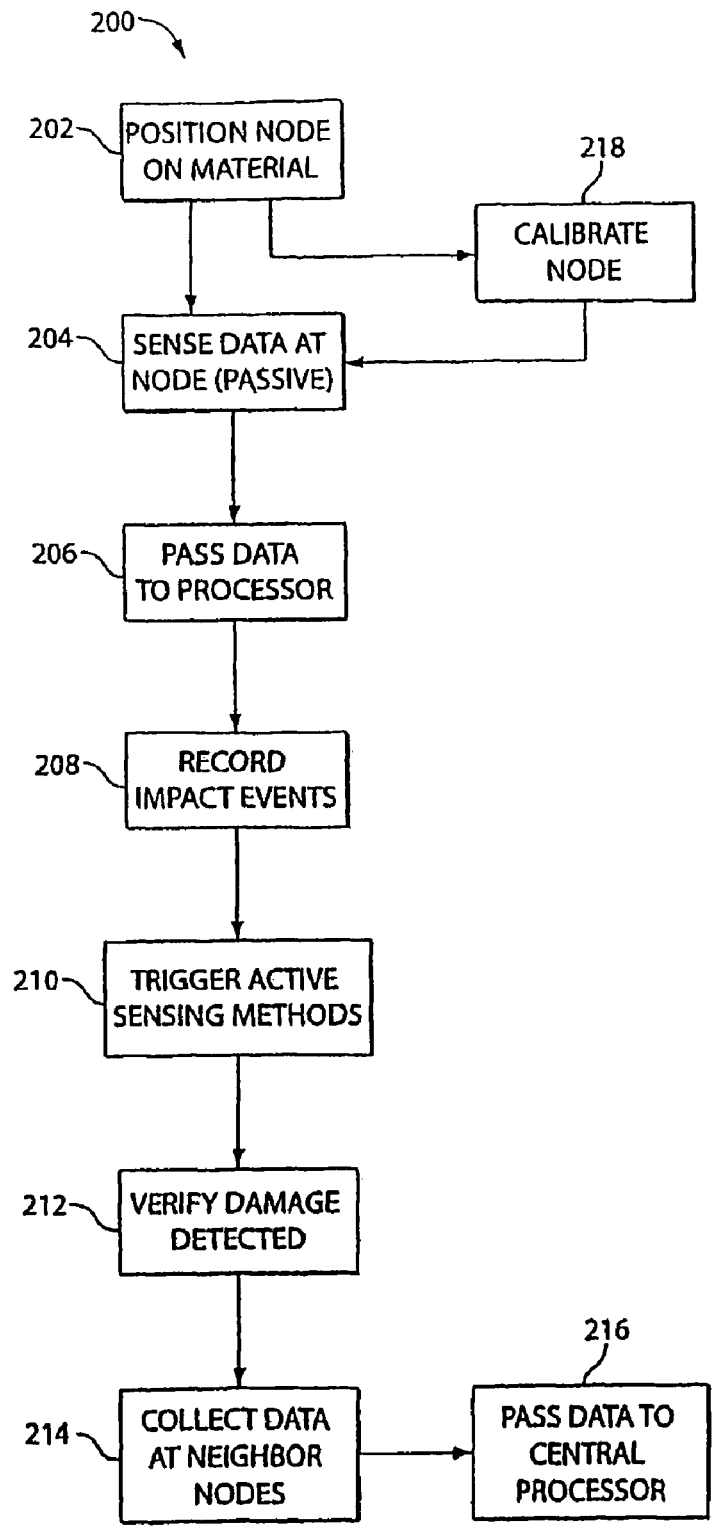
FIG. 7 is a flow chart of a process of using a device as in FIG. 1.

In operation, referring to FIG. 7, with further reference to FIGS. 1-6, a process 200 for detecting damage in a material or structure using a node 5 includes the stages shown. The process 200, however, is exemplary only and not limiting. The process 200 may be altered, e.g., by having stages added, removed, or rearranged.

At stage 202, a node 5 is positioned on the surface of a material or a structure for which structural integrity is to be tested or monitored. Preferably, a plurality of nodes are distributed throughout a structure and work in tandem. The node 5 can alternatively be embedded in a material or structure to conduct detection. Although the system can operate continuously, the system can be accessed by individuals to perform inspections on demand.

At stage 204, the node 5 collects data related to the structure to which it is affixed. The node 5 can collect data passively, for example, using strain and acoustic emission methods. Passive damage detection methods can be used continuously to sense the presence of damage in the structure. Passive methods are generally those that operate by detecting responses due to perturbations of ambient conditions. Strain monitoring is used to record strains over design limits, and can also be used to trigger more sophisticated detection methods. By analyzing the data at smaller time scales, acoustic emission can be performed passively to detect and record impact events and approximate the energy of impact. The nodes 5 pass the collected information to a local processing unit at stage 206.

Abnormal strain and/or acoustic events are recorded, as shown at stage 208. Conditions that differ from the ambient conditions of a structure can be recorded and further analyzed. To determine damage, comparison is made with a baseline measurement.

Where abnormal events have been detected, an active sensing method is triggered at the node 5, stage 210. When abnormal data is encountered, active methods such as frequency response and Lamb wave techniques are initiated. Active methods are used to give more information about the type, severity and location of damage. Active methods, for example, use an externally supplied energy in the form of a stress or electromagnetic wave to function. Examples of active methods include, but are not limited to, electrical and magnetic impedance measurements, eddy currents, optical fibers that use a laser light source, modal analysis and Lamb wave propagation. Active methods can be triggered by an event detected by the passive methods. Alternatively or concurrently, active methods can be performed at pre-set time intervals or initiated by an operator.

At stage 212, data from the active sensing mode is collected to verify damage. In a system that employs more than one node 5 for detection, once a single node 5 has collected damage, data is collected by nearby nodes in order to help confirm the presence and severity of damage, stage 214. At stage 216, the data is passed from node 5 to node 5, and to a central processing unit to be interpreted. For example, all of the data can be passed from each node 5. Data can be passed in a fire brigade fashion, such that substantially all data is passed from node to node within the system. The damage type, severity, and location can be communicated to other individuals, as can suggested actions.

In some methods of the invention, fixed spacing between the actuator 51 in a first node 5 and the sensor 50 in a second node 5 can be used to calculate wave speed in a material at the material's present state. The wave speed calculation self-calibrates the system and may reduce the need for analytically derived wave speed calculations to be determined. The calibration process can take place prior to each test measurement. Based on the calibration process, the system is self-compensating for the effects of temperature, humidity, strain or creep. For example, the fixed distance between the actuator and the sensor divided by the time of flight of the wave between the actuator and the sensor determines wave speed. The wave can be, for example, a surface, shear, Raleigh, Lamb or other type of wave for use in calculating wave speed. Self-compensation can be used to determine the state of the structure, e.g., thermal, hygral or strain. Also, by measuring the impedance and other signature data such as total energy and frequency spectrum of the actuator while being excited, a self-diagnostic can be performed to detect irregular operation.

Active Damage detection methods can be performed by using either a single damage detection node 5, or a network of several devices 5 working independently or in collaboration. When using a single node 5, a pulse-echo type of operation is used, where the structure being monitored or tested is excited by an actuator, and a response or reflections are measured by a co-located sensor. In the case of using multiple nodes 5, damage detection can also be performed by pulse-echo, whereas each node 5 independently collects response or reflection data, which is fused together to map out damage locations. Alternatively, when using more than one node 5, a pitch-catch method can also be used, whereas an actuator from one node 5 excites the structures being monitored or tested, and sensors from one or more other device nodes 5 measure the transmitted response to determine the state of the structure. The device 5 at which the actuation occurs is referred to as the master node. When using the pitch-catch method, the master node designation is iteratively cycled through each of the various nodes 5 so that combinations of transfer functions can be collected. The preferred method is to employ both of the pulse-echo and pitch-catch methods simultaneously. This case is similar to the previously described pitch-catch only method, however in this case reflected data from the master node sensor is also collected to be fused with all of the other data.

The structural monitoring tests are facilitated with the electronics on the PCB 22. The microprocessor initiates testing by triggering the arbitrary function generator to excite the actuator in the node 5 and initiating data collection by the datalogger on the PCB 22. The tests can be initiated remotely by a user, pre-programmed to be executed at certain intervals, or be triggered by passive methods. Digital data from the buffer is collected by a central processor via the wired or wireless data link. The data is processed by the central processor. The microprocessor on the PCB 22 can provide processing to locally assess damage.

Once voltage data has been collected by one of the methods previously described, there are a variety of ways this data can be decomposed in order to ascertain the state of the structure. First data can be filtered and de-noised using bandpass filters in order to remove high frequency electrical noise and low frequency drift and mechanical vibrations. Algorithms can be used that compare the integrated energy levels received at the sensors to determine if damage is present; increased reflected energy and decreased transmitted energy are both metrics of damage. This is followed by an evaluation of reflection time of flight, in order to determine the damage location by multiplying these results by the wave velocity. A fast-Fourier-transform can be performed to inspect the resulting frequency bandwidth, which is used to determine the type of damage present in the structure. By using three separate sensor physics to evaluate the damage, for example, one can minimize the occurrence of false positives.

In a system of damage detection devices embodied in a structure, actuation of the detection device 5 occurs at a master node. Sensing occurs at all other nodes. Use of a single master node distance to damage can be estimated, and the angle from the master node at which damage has been detected can also be estimated. The damage detection procedure can be run iteratively making each node a master node. With the use of multiple nodes, damage can be triangulated.

The invention provides an infrastructure to a sensor or actuator that operates using a compatible power source, such as piezoelectric, foil resistive, MEMS or eddy current, for example. The infrastructure described herein provides a "black-box" infrastructure allowing data and power to flow in and out of a distributed network of daisy-chained sensors, reducing cabling, time of installation, and cost. The infrastructure can be mass-produced at a low cost, and customized for applications in software. The device can be used to perform damage detection methods such as Lamb wave, Frequency response, Acoustic emission and strain/stress monitoring for any known material or structure.

Those skilled in the art will recognize, or be able to ascertain using no more than routine experimentation, numerous equivalents to the specific procedures described herein. Such equivalents are considered to be within the scope of the invention. Various substitutions, alterations, and modifications may be made to the invention without departing from the spirit and scope of the invention. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

The invention claimed is:

1. A device for use in detecting an event in a structure, the device comprising:
    a sensor encapsulation configured to be attached to the structure, the encapsulation containing:
        a sensor;
        an actuator positioned substantially in-plane to the sensor within the encapsulation, the actuator substantially completely surrounding the sensor; and
        a printed circuit board in communication with at least one of the sensor and the actuator, the printed circuit board comprising:
            a microprocessor constructed and arranged to collect data from at least one of the sensor and the actuator;
            a signal generator constructed and arranged to provide excitation to at least one of the sensor and the actuator; and
            an amplifier to condition the excitation.

2. The device of claim 1 wherein the microprocessor is configured to collect analog data from at least one of the sensor and the actuator, and further configured to convert the analog data to digital data.

3. The device of claim 1 further comprising a wireless chip coupled to the microprocessor.

4. The device of claim 1 further comprising a battery configured to provide power to the device.

5. The device of claim 1 further comprising a network connection configured to network multiple ones of the device.

6. A device for use in detecting an event in a structure, the device comprising:
    a sensor encapsulation configured to be attached to the structure, the encapsulation containing:
        a sensor;
        an actuator positioned substantially in-plane to the sensor within the encapsulation,
        wherein the sensor substantially completely surrounds the actuator; and
        a printed circuit board in communication with at least one of the sensor and the actuator, the printed circuit board comprising:
            a microprocessor constructed and arranged to collect data from at least one of the sensor and the actuator;
            a signal generator constructed and arranged to provide excitation to at least one of the sensor and the actuator; and
            an amplifier to condition the excitation.

7. The device of claim 6 wherein the microprocessor is configured to collect analog data from at least one of the sensor and the actuator, and further configured to convert the analog data to digital data.

8. The device of claim 6 further comprising a wireless chip coupled to the microprocessor.

9. The device of claim 6 further comprising a battery configured to provide power to the device.

10. The device of claim 6 further comprising a network connection configured to network multiple ones of the device.

11. A device for use in detecting an event in a structure, the device comprising:
    a sensor encapsulation configured to be attached to the structure, the encapsulation containing:
        a plurality of sensors;
        a wireless chip;
        an actuator positioned substantially in-plane to the plurality of sensors within the encapsulation; and
        a printed circuit board in communication with the wireless chip and at least one of the plurality of sensors and the actuator, the printed circuit board comprising:
            a microprocessor constructed and arranged to collect data from at least one of the sensor and the actuator;
            a signal generator constructed and arranged to provide excitation to at least one of the sensor and the actuator; and
            an amplifier to condition the excitation,
    wherein the plurality of sensors are co-located on at least one piezoelectric wafer,
    wherein the plurality of sensors are collectively at least partially surrounded by the actuator.

12. The device of claim 11 further comprising a battery configured to provide power to the device.

13. The device of claim 11 wherein the wireless chip is configured to provide a network connection between multiple ones of the device.

14. A device for use in detecting an event in a structure, the device comprising:
    a sensor encapsulation configured to be attached to the structure, the encapsulation containing:
        a sensor;
        a wireless chip;
        a plurality of actuators positioned substantially in-plane to the sensor within the encapsulation; and
        a printed circuit board in communication with the wireless chip and at least one of the sensor and the plurality of actuators, the printed circuit board comprising:
            a microprocessor constructed and arranged to collect data from at least one of the sensor and the plurality of actuators;

a signal generator constructed and arranged to provide excitation to at least one of the sensor and the plurality of actuators; and
an amplifier to condition the excitation;
wherein the plurality of actuators are co-located on at least one piezoelectric wafer,
wherein the plurality of actuators are collectively at least partially surrounded by the sensor.

15. The device of claim 14 further comprising a battery configured to provide power to the device.

16. The device of claim 14 wherein the wireless chip is configured to provide a network connection between multiple ones of the device.

* * * * *